(12) United States Patent
Davies et al.

(10) Patent No.: US 6,294,152 B1
(45) Date of Patent: Sep. 25, 2001

(54) IRON(III) COMPLEXES AS CONTRAST AGENTS FOR IMAGE ENHANCEMENT IN MAGNETIC RESONANCE IMAGING

(75) Inventors: Julian A. Davies, Sylvania, OH (US); Wolfgang Ebert, Berlin (DE); Bernd Raduechel, Berlin (DE); Heribert Schmitt-Willich, Berlin (DE)

(73) Assignees: The University of Toledo, Toledo, OH (US); Schering Aktiengesellschaft of Germany ( * ) Notice: Subject to any disclaimer, the term of this patent is extended or adjusted under 35 U.S.C. 154(b) by 0 days.

(21) Appl. No.: 09/227,961

(22) Filed: Jan. 11, 1999

(51) Int. Cl.$^7$ .................................................. A61B 5/055
(52) U.S. Cl. ........................................................ 424/9.361
(58) Field of Search ........................... 424/9.361; 546/5, 546/296

(56) References Cited

U.S. PATENT DOCUMENTS

| | | | |
|---|---|---|---|
| 4,585,780 | * 4/1986 | Hider et al. | 514/348 |
| 4,650,793 | * 3/1987 | Hider et al. | 514/188 |
| 4,689,041 | 8/1987 | Corday et al. | 604/53 |
| 4,731,239 | 3/1988 | Gordon | 424/9 |
| 4,880,008 | 11/1989 | Lauffer | 128/654 |
| 5,010,191 | 4/1991 | Engelstad et al. | 544/225 |
| 5,185,319 | * 2/1993 | Hider et al. | 514/3 |
| 5,225,282 | 7/1993 | Chagnon et al. | 428/407 |
| 5,256,676 | * 10/1993 | Hider et al. | 514/348 |
| 5,494,656 | 2/1996 | Davies | 424/9.364 |
| 5,624,901 | 4/1997 | Raymond et al. | 514/17 |

FOREIGN PATENT DOCUMENTS

| | | |
|---|---|---|
| 89/11873 * 12/1989 | (WO) . | |
| WO 92/09884 6/1992 | (WO) | G01N/24/00 |
| WO 95/07653 3/1995 | (WO) | A61B/5/055 |

OTHER PUBLICATIONS

Davies et al., "Iron–based second–sphere contrast agents for magnetic resonance imaging . . . ", Academic Radiology, vol. 3, pp. 936–945 (1996).

Dobbin et al., "Synthesis, physicochemical properties and biological evaluation of N–substituted 2–alkyl–3–hydroxy–4(1H)–pyridinones . . . ", Journal of Medicinal Chemistry, vol. 36, pp. 2448–2458 (1993).

Rajan et al., "Metal Chelates of L–Dopa . . . ", Brain Research, vol. 107, pp. 317–331 (1976).

Lauffer, "Paramagnetic Metal Complexes . . . ", Chem. Rev., vol. 87, pp. 901, 908, 921 and 922 (1987).

Bagyinka et al., "The pH Dependence . . . ", Proc. –Int. Conf. Moessbauer Spectrosc., vol. 1, pp. 305–306 (1977) (Abstract).

Rudzitis, "Chelates of 2,4–Dihydroxydithiobenzoic . . . ", Latv. PSR Zinat. Akad. Vestis, Kim. Ser., vol. 5, pp568–571 (1971) (Abstract).

\* cited by examiner

Primary Examiner—Michael G. Hartley
(74) Attorney, Agent, or Firm—MacMillan, Sobanski & Todd, LLC

(57) ABSTRACT

A compound of formula (I):

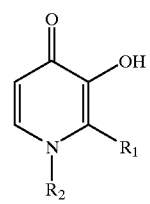

(I)

wherein, $R_1$ is independently selected from methyl and ethyl and $R_2$ is independently selected from hydrogen, alkyl, and substituted alkyl. The compound is capable of functioning as a ligand and complexing with paramagnetic Fe(III) ion for use as a second-sphere contrast enhancing agent for magnetic resonance imaging of tissue. The present invention also relates to a method of administering the second sphere contrast agent.

2 Claims, 4 Drawing Sheets

Percent enhancement of the liver (square symbols) and the kidneys (diamond symbols) of a rat after injection with the tris(ligand) iron(III) complex of ligand VIII, Fe-BETALA.

(dose : 100 μmol / kg bw)

Percent enhancement of the liver (square symbols) and the kidneys (diamond symbols) of a rat after injection with the tris(ligand) iron(III) complex of ligand VI, Fe-ETOHMAL.

(dose : 100 μmol / kg bw)

Percent enhancement of tumor (diamond symbols) and the muscle (triangle symbols) of a rat after injection with the tris(ligand) iron(III) complex of ligand XI, Fe-PYRMAL.

(dose : 50 µmol / kg bw)

Percent enhancement of tumor (diamond symbols) and the muscle (triangle symbols) of a rat after injection with the tris(ligand) iron(III) complex of ligand XX, Fe-ETPYRMAL.

(dose : 50 μmol / kg bw)

IRON(III) COMPLEXES AS CONTRAST AGENTS FOR IMAGE ENHANCEMENT IN MAGNETIC RESONANCE IMAGING

FIELD OF THE INVENTION

This invention relates generally to compounds capable of complexing with paramagnetic Fe(III) ion useful as contrast agents for image enhancement in magnetic resonance imaging. More particularly, this invention is directed to tissue-specific, second-sphere complexes comprising Fe(III) complexes of 1-substituted-3-hydoxy-2-alkyl-4-pyridinone ligands, and to a method for performing magnetic resonance imaging of a patient using the second-sphere complexes.

BACKGROUND OF THE INVENTION

Magnetic resonance imaging (MRI) is a nuclear magnetic resonance (NMR) technique that may be used clinically to differentiate between normal and abnormal tissues. The $^1$H NMR imaging method is based upon differences in water proton concentrations and relaxation rates within different tissue types.

When magnetic resonance imaging was first being developed as a diagnostic tool, it was believed that there would be no need for a contrast agent and, that by the use of carefully selected pulse sequences, it would be possible to differentiate tissue types and provide accurate diagnoses. See, Wolf, C. L., Burnett, K. R, Goldstein, U. & Joseph P. M. Magn. Res. Ann. 1985, 231. In many areas of diagnostic medicine this has been found not to be the case, leading to contrast agents being developed.

Contrast agents function in such a way that they lead to the alteration of an image so that, if localized within, say, a tumor, the signal intensity due to the water protons within the tumor becomes different from that of the surrounding tissue. There are two ways in which these alterations can be made. The signal can become brighter or the signal can become darker, and both of these effects are obtainable using various types of contrast agents.

Nearly all of the classes of contrast agent create their desired effect by changing the spin-lattice relaxation time ($T_1$) and/or the spin-spin relaxation time ($T_2$) of the water protons (one notable exception is the family of diamagnetic fluorocarbons, which function by replacing water, thus leading to a null signal for that region). See, Wood, M. L. & H. P. A. J. Mag. Reson. Imag. 1993, 3, 149. See, Lauffer, R. B. Invest. Radiol. 1990, 25, S32. Those contrast agents that operate predominantly on spin-spin relaxation times are the superparamagnets, such as particulate iron oxides. Those contrast agents that operate predominantly on the spin-lattice relaxation time are the paramagnets. These species possess unpaired electrons and thus have a net magnetic moment. It is this magnetic moment which leads to an increase in the spin-lattice relaxation rate of water protons, as the magnetic moment stimulates the transition from a high-energy spin state to a lower energy spin state. For contrast-enhanced MR imaging it is desirable to have a large magnetic moment, with a relatively long electronic relaxation time. Based upon these criteria, candidates for use in contrast agents include Gd(III), an $f^7$ system, and the $d^5$ systems Mn(II) and high-spin Fe(III). Gadolinium(III) has the largest magnetic moment among these three and it has been extensively studied.

It might seem that the aqua ion of each of these paramagnetic metals would be a good choice for use as a contrast agent, as these have the largest possible number of bound water molecules. However, the aqua ions are relatively toxic, and there exists little opportunity to control the biodistribution of these species. The reported $LD_{50}$ values for the metal chloride salts in aqueous solution are 1.4, 1.5 and 1.6 mmol/kg for gadolinium, manganese and iron respectively when administered to mice i.p. See, Lauffer, R. B. Chem. Rev. 1987, 87, 901.

In attempts to solve both of these problems, a variety of ligands—organic molecules which are able to coordinate to the metal ions—have been employed. For current clinical contrast agents that are based on gadolinium, ligands are employed which occupy almost all of the coordination sites on the metal ion, typically leaving one site available for water molecules to reversibly bind. This approach reduces the toxicity of the metal ion and, by careful variation of the ligand system, potentially allows control of the biodistribution such that in vivo targeting may be achieved. Other desirable properties of a potential contrast agent may include prompt clearance of an extracellular agent as well as in vivo and in vitro stability.

It will be appreciated that there are potential advantages with the use of manganese and iron in comparison to gadolinium because both iron and manganese have a natural human biochemistry which may make it simpler to design target-specific contrast agents based on known biochemical uptake mechanisms, i.e., tissue specificity.

Another problem to overcome is the choice of ligand system. More particularly, it is desirable to provide a ligand system that will reduce the toxicity to an acceptable level, and give the desired in vivo targeting.

It will be appreciated from the foregoing that there is still a significant need for a tissue-specific contrast agent for image enhancement in magnetic resonance imaging that addresses at least some of the problems of the prior art. It is another object of the present invention to provide a tissue-specific contrast agent for image enhancement in magnetic resonance imaging having toxicity levels no greater than clinical agents currently used, e.g., Gd-DTPA (gadolinium ion chelated with the ligand diethylenetriaminepentaacetic acid). Yet another object of the present invention is to provide a tissue-specific contrast agent for image enhancement of tumors. Another object of the present invention is to provide a tissue-specific contrast agent for image enhancement to provide precise localization and sizing of the tissue.

SUMMARY OF THE INVENTION

Briefly, in accordance with the present invention, there is provided a compound of formula (I):

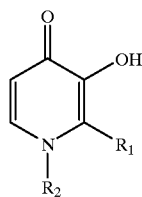

(I)

wherein, $R_1$ is independently selected from methyl and ethyl and $R_2$ is independently selected from hydrogen, alkyl and substituted alkyl. The substituent may be independently selected from one or more hydroxyl groups, carboxylic acid groups, ether linkages, amine functionality or a heterocyclic ring. The compound is capable of functioning as a ligand and complexing with paramagnetic Fe(III) ion for use as a second-sphere contrast enhancing agent for magnetic resonance imaging of tissue.

Also contemplated by the present invention is a method for magnetic resonance image enhancement utilizing the contrast agents, and a method of administering the second-sphere contrast agents.

BRIEF DESCRIPTION OF THE DRAWINGS

Further features and other objects and advantages of this invention will become clear from the following detailed description made with reference to the drawings in which.

DETAILED DESCRIPTION OF THE PREFERRED EMBODIMENT

Figure 1:
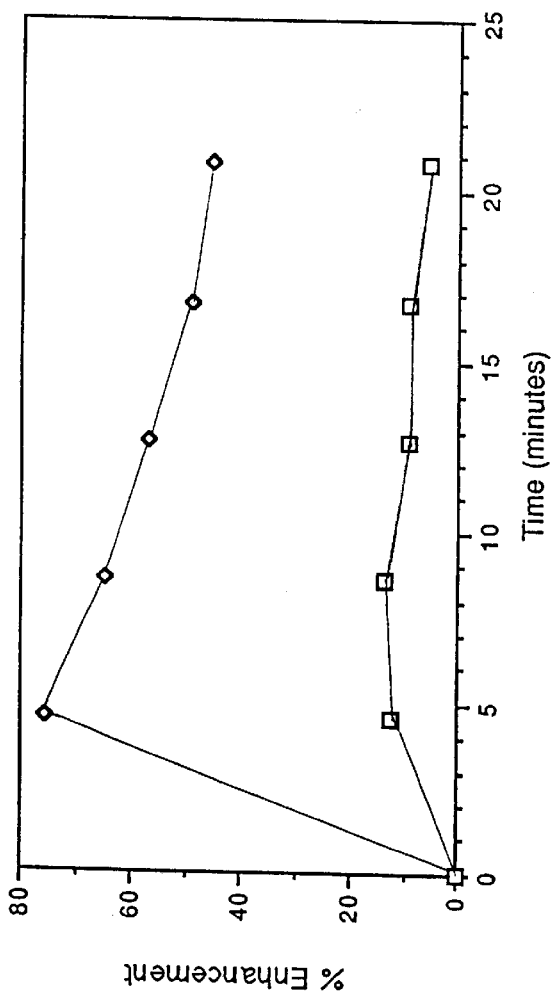
FIGS. 1 and 2 are plots of percent enhancement of the liver and kidney of a rat versus time after injection of the contrast agent.

The development of pharmaceutical agents which enhance image contrast between tissue types presents unique challenges since such agents are not themselves imaged but rather function through affecting water molecule proton relaxation rates. This important distinction between magnetic resonance imaging contrast agents and other types of clinically useful diagnostic pharmaceuticals, such as for example X-ray contrast agents or radiopharmaceuticals, leads to major differences in the in vivo distribution requirements of each type of agent. Thus, for a magnetic resonance imaging contrast agent to be effective, it is required that the water proton relaxation rate in the target tissue is affected differently from the relaxation rate of the water protons in the surrounding tissue. Such differentiation is possible because of the mode of action of these image enhancement agents. Paramagnetic species, such as certain complexes of metal ions, can alter the longitudinal and/or transverse relaxation rates of adjacent nuclei by dipolar interactions.

The present invention is directed to a class of magnetic resonance imaging contrast agents displaying important properties in medical diagnosis. More particularly, the present invention is directed to a class of magnetic resonance imaging contrast agents that accumulates in tissue, such as tumor tissue. The class of magnetic resonance imaging contrast agents comprises a complex of paramagnetic ions chelated with ligands of formula (I):

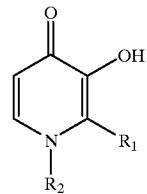

(I)

wherein, $R_1$ is selected independently from methyl and ethyl and $R_2$ is selected independently from hydrogen, alkyl and substituted alkyl. The substituent may be independently selected from one or more hydroxyl groups, carboxylic acid groups, ether linkages, amine functionality or a heterocyclic ring.

The metal ion with the most suitable magnetic moment and relaxation efficiency for this purpose is Fe(III). In order for the Fe(III) metal ion to enhance the relaxation rate of water protons in tissue, it is important that the water molecules approach close to the paramagnetic center.

It is believed that three basic types of interactions between the metal ion and water molecules may occur. In an inner-sphere interaction, water molecules bind to and exchange with the metal ion, for a very effective contact. In an outer-sphere interaction, all of the Fe(III) metal ion coordination sites are occupied by a set of ligands, and so water molecules are affected only through translational diffusion past the paramagnetic center. In an intermediate case, i.e., second-sphere interaction, the Fe(III) metal ion is surrounded by a set of ligands which prevent direct coordination of water molecules to the metal ion. However, the ligands of a second-sphere complex also provide bonding sites for the hydrogen bonding of water molecules thereto.

Fe(III) metal ions which interact with water molecules by an inner-sphere mechanism are very effective for enhancing relaxation rates, but such ions generally exhibit very high toxicities. The origin of this toxicity may lie in the availability of coordination sites at the Fe(III) metal ion center which leads to binding by not only water molecules but also by activated oxygen, nitrogen or sulfur groups of a number of biomolecules. The coordination sites at the metal center can essentially be removed by using a suitable set of ligands. However, although this reduces toxicity, it typically leaves only the less-effective, outer-sphere interactions with water molecules to provide relaxation rate enhancement. To balance these effects, the complexes in accordance with the present invention are designed to operate primarily by second-sphere interactions and have been developed for use in magnetic resonance imaging.

The ligands useful for second-sphere relaxation enhancement must meet specific requirements. They must bind strongly to paramagnetic Fe(III) ions, since ligand dissociation would result in metal ion toxicity and ligand-derived organic toxicity. Useful ligands must form complexes which are excreted efficiently to prevent long-term toxicity by, for example, the accumulation in lipophilic membranes or retention by cells in the reticular endothelial system. Moreover, the useful ligands must provide sites for the hydrogen bonding of water molecules.

In accordance with the present invention the ligands are of formula (I):

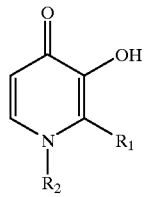
(I)

wherein, $R_1$ is selected independently from methyl and ethyl and $R_2$ is selected independently from hydrogen, alkyl and substituted alkyl. The substituent may be independently selected from one or more hydroxyl groups, carboxylic acid groups, ether linkages, amine functionality or a heterocyclic ring.

Preferred embodiments of the ligands are of formulas (II)–(XXIII).

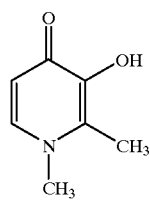
(II)

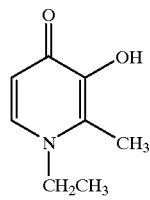
(III)

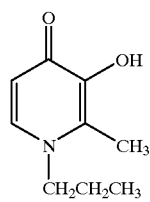
(IV)

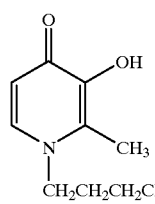
(V)

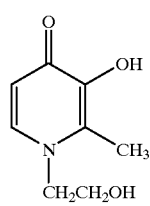
(VI)

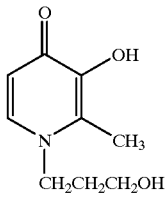
(VII)

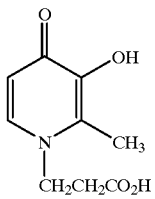
(VIII)

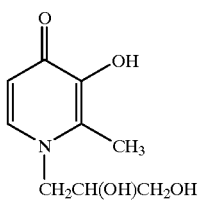
(IX)

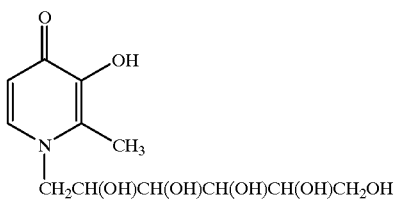
(X)

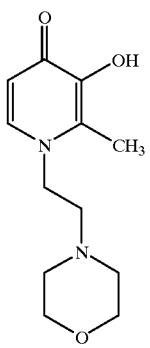
(XI)

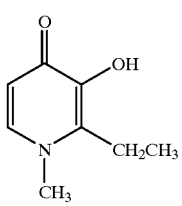
(XII)

(XIII)
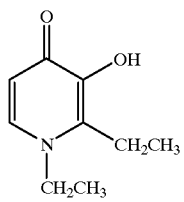

(XIV)
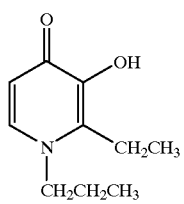

(XV)
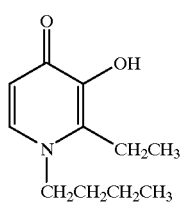

(XVI)
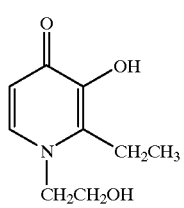

(XVII)
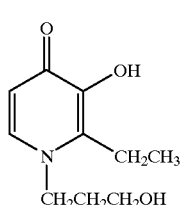

(XVIII)
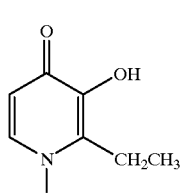

(XIX)
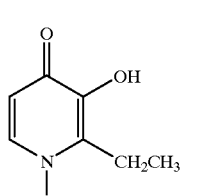

(XX)
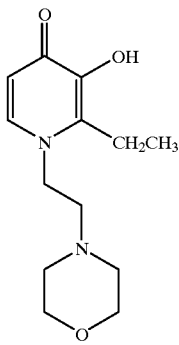

(XXI)
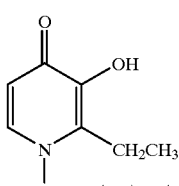

(XXII)
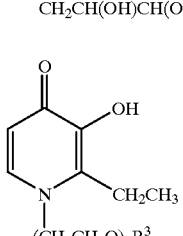

wherein n is between 2 and 120 and $R^3$ is independently selected from hydrogen or methyl.

(XXIII)
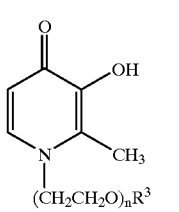

wherein n is between 2 and 120 and $R^3$ is independently selected from hydrogen or methyl.

The mechanism of efficient excretion of the Fe(III) metal ion complexes from the body, which preferably should occur within a few hours following administration, is less-well understood. Only certain broad principles are available to assist in the complex design. Thus, the presence of highly charged and/or hydrogen bonding groups and the absence of lipophilic side chains minimizes interactions with membranes, plasma proteins, etc., and so allows for effective renal excretion. Certain anionic complexes are excreted by the hepatobiliary pathway in competition with excretion via the kidneys. Thus to avoid-long term toxicity, the factors promoting excretion must be examined.

The presence of hydrogen bonded water molecules is required for the operability and utility of second-sphere contrast agents complexes, according to the present invention. Complexes that fall into this group rely primarily on the hydrogen bonding of water molecules to the heteroatoms that form the paramagnetic Fe(III) metal ion-to-ligand linkages.

The second-sphere complexes of the present invention comply with the requirements set forth above. The inventive complexes are prepared utilizing paramagnetic Fe(III) metal ions, which are detectable in their chelated form by magnetic resonance imaging.

Suitable ligands for preparing the second-sphere complexes according to the present invention include ligands where the ligands are of the general formula (I):

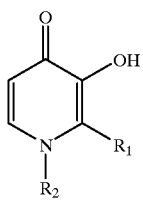

(I)

wherein, $R_1$ is selected independently from methyl and ethyl and $R_2$ is selected independently from hydrogen, alkyl and substituted alkyl. The substituents may be independently selected from one or more hydroxyl groups, carboxylic acid groups, ether linkages, amine functionality or a heterocyclic ring.

The second-sphere complexes of the present invention may be administered in any convenient manner to the subject. For example, the complexes may be dissolved in a saline solution and injected intravenously or subcutaneously. Generally, the dosages will be limited to only those amounts necessary and sufficient to allow detection by magnetic resonance imaging. Such dosages typically range from about 0.02 mmol/kg to about 0.5 mmol/kg. Preferably, the dosages range from about 0.05 mmol/kg to about 0.15 mmol/kg.

The second-sphere complexes of the present invention enhance magnetic resonance imaging conducted utilizing conventional nuclear magnetic resonance devices. The complexes shorten the imaging time required to produce and maintain images of the target tissues.

The invention will be further clarified by a consideration of the following examples, which are intended to be purely exemplary of the invention.

Ligand Synthesis

2-Methyl-3-(benzyloxy)-4-pyranone. In a solution of methanol (180 mL) 3-hydroxy-2-methyl-4-pyranone (19.6 g) was dissolved, followed by the addition of sodium hydroxide (6.0 g) in water (20 mL). Benzyl chloride was added (19.0 g) and the solution was placed under conditions of reflux for 6 hours. After this time the solvent was removed by rotary evaporation to leave an orange oil. This oil was dissolved in methylene chloride and washed twice with 5% aqueous sodium hydroxide (75 mL), then twice more with water (75 mL). The organic layer was rotary evaporated to an orange oil (27.6 g).

3-Hydroxy-1,2-dimethyl-4-pyridinone (LIGAND II). 2-methyl-3-(benzyloxy)-4-pyranone (10.4 g) was dissolved in water (80 mL) and ethanol (80 mL). Methylamine hydrochloride (4.9 g) was dissolved in water (50 mL) and sodium hydroxide was added (2.9 g). This solution was added to the solution of 2-methyl-3-(benzyloxy)-4-pyranone, followed by the addition of 2N sodium hydroxide (4.0 mL). This solution was placed under conditions of reflux for 18 hours. After this time, the pH of the solution was set to 1.1 with hydrochloric acid, and the solution was concentrated. Water was added (80 mL), and the sample was washed with diethyl ether. The resulting precipitate was dissolved in ethanol, and the pH was set to 7.8 with 10N sodium hydroxide. The solution was extracted three times with methylene chloride, and these aliquots were combined and dried over sodium sulfate. After decanting, the solvent was removed by rotary evaporation, resulting in an orange oil. This oil was dissolved in ethanol and hydrochloric acid, and the solvent was removed by rotary evaporation, resulting in a yellow solid. This solid was recrystallized from ethanol and diethyl ether resulting in a white powder. This solid was dissolved in ethanol (70 mL) and water (5 mL) and 5% palladium on charcoal catalyst (0.26 g) was added. The resulting mixture was placed under 1 atm. of hydrogen for 12 hours. Following filtration, the solvent was removed by rotary evaporation resulting in a white solid. This was recrystallized from ethanol and diethyl ether, resulting in a white powder (2.1 g). Proton NMR ($D_2O$): 7.79 (d, 1H), 6.89 (d, 1H), 3.79 (s, 3H). 2.38 (s, 3H).

1-Ethyl-3-hydroxy-2-methyl-4-pyridinone (III). A reaction analogous to that used for the synthesis of 3-hydroxy-1,2-dimethyl-4-pyridinone was employed, starting with 70% ethylamine (4.6 g). No precipitate was observed after concentration. Recrystallization from ethanol and diethyl ether resulted in a white powder (4.2 g). Proton NMR ($D_2O$): 7.85 (d, 1H), 6.88 (d, 1H), 4.12 (q, 2H), 2.36 (s, 3H), 1.24 (t, 3H).

1-Butyl-3-hydroxy-2-methyl-4-pyridinone (LIGAND V). A reaction analogous to that used for the synthesis of 3-hydroxy-1,2-dimethyl-4-pyridinone was employed, starting with butylamine (5.3 g). No precipitate was observed after concentration. Recrystallization from ethanol and diethyl ether resulted in a white powder (4.5 g). Proton NMR ($D_2O$): 7.84 (d, 1H), 6.80 (d, 1H), 4.15 (q, 2H), 2.39 (s, 3H), 1.61 (m, 2H), 1.16 (m, 2H), 0.72 (t, 3H).

1-(2'-Hydroxyethyl)-3-hydroxy-2-methyl-4-pyridinone (LIGAND VI). A reaction analogous to that used for the synthesis of 3-hydroxy-1,2-dimethyl-4- pyridinone was employed, starting with ethanolamine (0.44 g). No precipitate was observed after concentration. Recrystallization from ethanol and diethyl ether resulted in a white powder (0.53 g). Proton NMR ($D_2O$): 7.82 (d, 1H), 6.89 (d, 1H), 4.27 (t, 2H), 3.74 (t, 2H), 2.36 (s, 3H).

1-(2'-Carboxyethyl)-3-hydroxy-2-methyl-4-pyridinone (LIGAND VIII). A reaction analogous to that used for the synthesis of 3-hydroxy-1,2-dimethyl-4-pyridinone was employed starting with β-alanine (2.5 g). No precipitate was observed after concentration and, at this point, the pH was set to 4 with hydrochloric acid. Following extraction with dichloromethane, the solvent was removed by rotary evaporation. Hydrogenolysis was performed as before, although the final product was not recrystallized. An off-white powder was obtained (2.3 g). Proton NMR ($D_2O$): 7.89 (d, 1H), 6.88 (d, 1H), 4.39 (t, 2H), 2.76 (t, 2H), 2.38 (s, 3H).

Other data from NMR, mass spectroscopy and elemental analysis confirmed the structural assignments made for the remaining ligands.

Other ligands were synthesized by similar methods.

Syntheses of Iron(III) Complexes

Iron(III) complexes for MR imaging experiments were prepared in two different ways:

A. Iron(III) solutions were prepared by dissolution of $FeCl_3$ in a small amount of distilled, deionized water with the amounts necessary of the appropriate ligand. The pH was adjusted to 7.2 with aqueous sodium hydroxide and/or hydrochloric acid. The volumes were adjusted with distilled, deionized water to give the desired concentrations for imaging experiments.

B. Iron(III) complexes were isolated as solid materials by reaction of iron(III) tris(acetylacetonate) with three molar equivalents of ligand in water containing three molar equivalents of NaOH at 80° C. Extraction with diethyl ether and/or methylene chloride to remove acetylacetone was followed by lyophilization to produce solid compounds. Molecular formulas were confirmed by elemental analysis. Solid compounds were dissolved in water to generate aqueous solutions for administration.

The X-ray crystal structure of the tris(ligand)iron(III) complex of ligand III, Fe-ETMAL, has been determined and reveals the presence of second-sphere water molecules hydrogen bonded to the oxygen atoms that form the iron-ligand linkage.

Imaging Experiments on Rats

Figure 2:
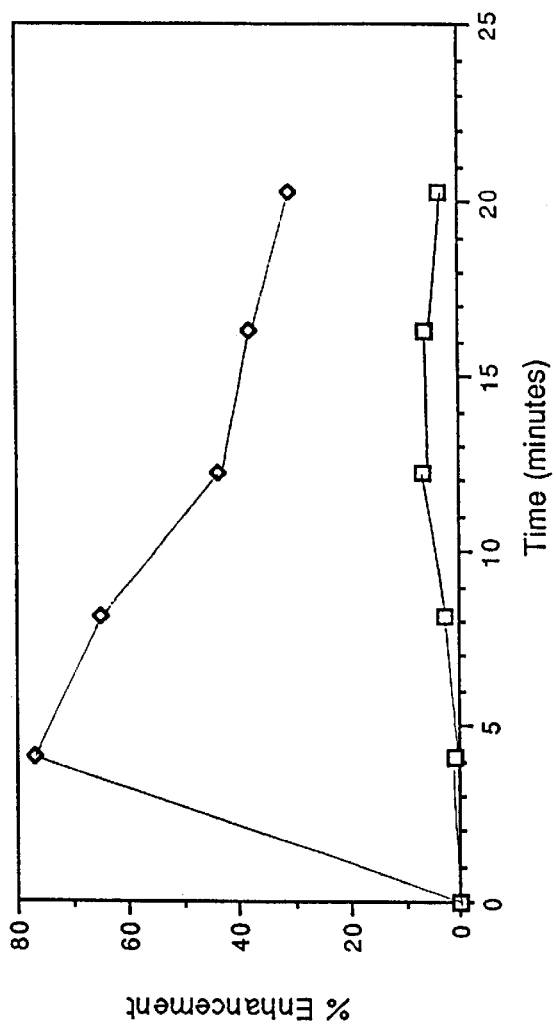

Animal studies were performed with a 1.5-T superconducting MR unit (Signal; GE Medical Systems) using a send-and-receive head coil containing two anesthetized female Fischer 344 rats. After a localizer image was obtained, a spin-echo pulse sequence was used with a 256×256 matrix (three signals acquired) over a 20-cm field of view with a thickness of 3 mm and a 1.5-mm intersection gap. The pulse sequence parameters were TR=300 ms and TE=20 ms. Sagittal images were collected before administration of the contrast agent and after administration, five more images were collected. Results for the tris(ligand)iron (III) complex of ligand VIII, Fe-BETALA, are shown in FIG. 1. Results for the tris(ligand)iron(III) complex of ligand VI, Fe-ETOHM,AL, are shown in FIG. 2.

Figure 3:
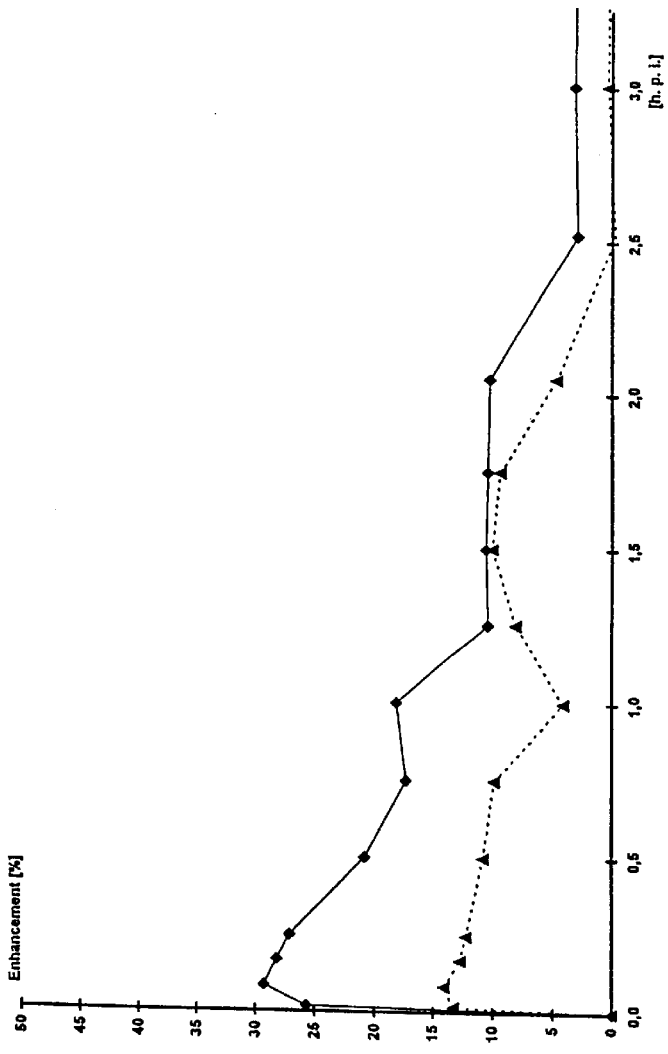
FIGS. 3 and 4 are plots of percent enhancement of muscle tissue and tumors in rats versus time after injection for three different contrast agents.
Figure 4:
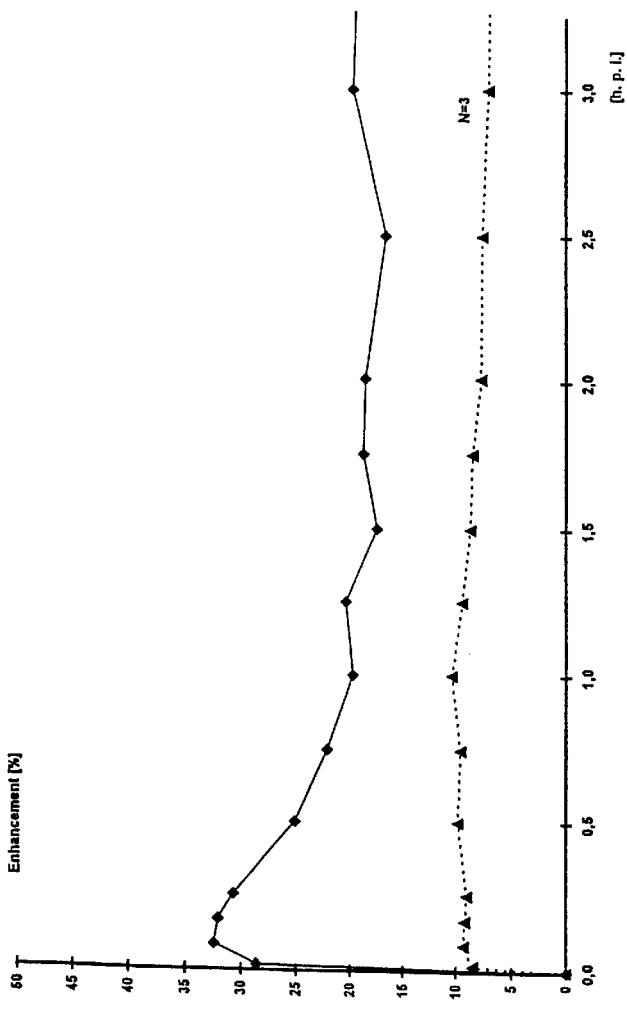

Imaging Experiments on Tumor-Bearing Rats $T_1$-weighted MRI examination (SE 400/15; SISCO SIS 85, 2 T) of the new MR contrast agents in rats (inbred Copenhagen, male, ca. 250 g bw) with implanted prostatic tumors (Dunning R3327, MAT/Lu) in the thigh muscles has been performed. Results for the tris(ligand) iron(III) complex of ligand XI, Fe-PYRMAL, are shown in FIG. 3. Results for the tris(ligand) iron(III) complex of ligand XX, Fe-ETPYRMAL, are shown in FIG. 4.

Toxicity Studies in Mice

The $LD_{50}$ value of the tris(ligand) iron(III) complex of ligand VI, Fe-ETOHMAL, has been determined i.v. in mice and found to be ca. 7.5 mmol/kg bw. The $LD_{50}$ value of the tris(ligand) iron(III) complex of ligand IX, Fe-DIOLMAL, has been determined i.v. in mice and found to be ca. 20.0 mmol/kg bw.

Relaxivity in Water and Plasma

Relaxivity values ($mM^{-1}s^{-1}$) have been determined in water and in plasma at 20 MHz and 37° C. Values obtained are shown in the Table immediately below:

| Ligand: | Tris(ligand)iron(III) complex of | |
| --- | --- | --- |
| | r1; r2 ($H_2O$) | r1; r2 (plasma) |
| VIII | 1.8, 1.8 | 2.1; 2.3 |
| VI | 1.7; 1.8 | 2.0; 1.9 |
| XI | 1.7; 1.8 | 2.3; 2.3 |
| X | 1.6; 1.7 | 2.2; 2.2 |

The documents, patents and patent applications referred to herein are hereby incorporated by reference.

Having described presently preferred embodiments of the invention, it is to be understood that it may be otherwise embodied within the scope of the appended claims.

What is claimed is:

1. A method for performing magnetic resonance imaging of tissue in a patient, comprising:

a) providing a second-sphere contrast enhancing agent, comprising a paramagnetic Fe(III) ion complexed with ligands of formula (I):

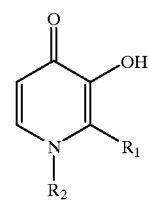

(I)

wherein, R1 is selected independently from methyl and ethyl and R2 is selected independently from hydrogen, alkyl and substituted alkyl, wherein the substituent may be selected independently from one or more hydroxyl groups, carboxylic acid groups, ether linkages, amine functionality or a heterocyclic ring, and wherein the ligands surround the Fe(III) ion and prevent direct coordination of water molecules to the Fe(III) ion, and wherein the ligands provide bonding sites for the hydrogen bonding of water molecules to the ligands;

b) administering the second-sphere contrast enhancing agent to the patient to enhance the nuclear magnetic resonance image of the tissue; and c) subjecting the patient to nuclear magnetic resonance imaging.

2. The method of claim 1 wherein the tissue comprises tumor tissue.

* * * * *